United States Patent [19]

Nigam

[11] Patent Number: 5,312,449
[45] Date of Patent: May 17, 1994

[54] IMPLANTABLE MEDICAL APPARATUS FOR STIMULATING A HEART

[75] Inventor: Indra Nigam, Santa Clarita, Calif.

[73] Assignee: Siemens Aktiengesellschaft, Munich, Fed. Rep. of Germany

[21] Appl. No.: 824,404

[22] Filed: Jan. 23, 1992

[30] Foreign Application Priority Data

Jan. 25, 1991 [SE] Sweden .................................. 9100229

[51] Int. Cl.⁵ ............................................ A61N 1/362
[52] U.S. Cl. .................................................... 607/14
[58] Field of Search ................... 128/419 PG, 419 D

[56] References Cited

U.S. PATENT DOCUMENTS

| | | | |
|---|---|---|---|
| 4,408,606 | 10/1983 | Spurrell et al. | 128/419 PG |
| 4,553,547 | 11/1985 | Keimel | 128/419 PG |
| 4,574,437 | 3/1986 | Segerstad et al. | 128/419 PG |
| 4,705,043 | 11/1987 | Imran | 128/419 PG |
| 4,870,974 | 10/1989 | Wang | 128/700 |

*Primary Examiner*—William E. Kamm
*Assistant Examiner*—Scott M. Getzow
*Attorney, Agent, or Firm*—Hill, Steadman & Simpson

[57] ABSTRACT

An implantable medical apparatus delivers, in order to induce or terminate a tachyarrhythmia in a heart, a sequence consisting of several stimulation pulses having a time interval $T_t$ between each stimulation pulse. The first stimulation pulse is delivered after the lapse of a time interval $T_t$, triggered by a spontaneous heart event If a detector in the apparatus detects a spontaneous heart event during any of the time intervals $T_t$ between the stimulation pulses during the attempt of inducing or terminating, the next stimulation pulse will be delivered after the lapse of the time interval $T_t$ from the detected spontaneous heart event. The apparatus also limits the duration of the sequence.

12 Claims, 2 Drawing Sheets

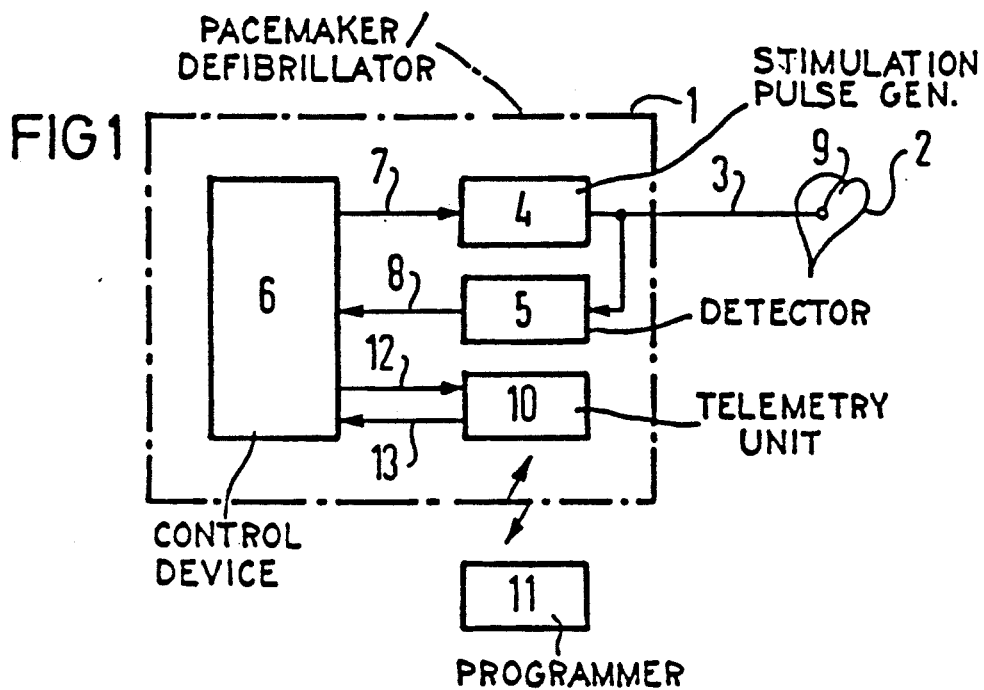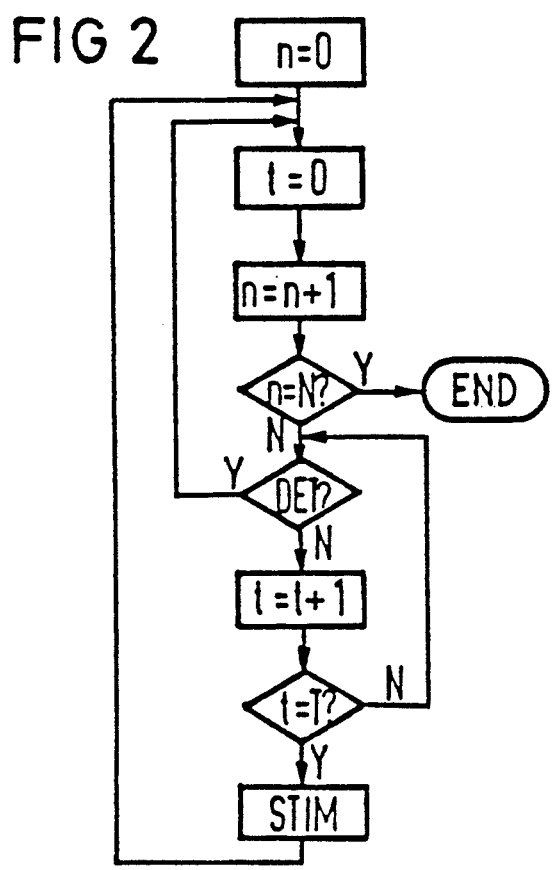

IMPLANTABLE MEDICAL APPARATUS FOR STIMULATING A HEART

BACKGROUND OF THE INVENTION

1. Field of the Invention

The invention relates to an implantable medical apparatus for stimulating a heart, of the type having a stimulation pulse generator which generates and delivers stimulation pulses, a detector which, when activated, detects spontaneous heart events and a control device which controls the stimulation pulse generator and the detector, which apparatus for inducing or terminating a tachyarrhythmia delivers a sequence consisting of a predetermined number of stimulation pulses with a time interval between each stimulation pulse, which sequence is released at a detection of a spontaneous heart event.

2. Description of the Prior Art

An apparatus of the type described above is disclosed in U.S. Pat. No. 4,705,043 which describes a cardioverter/pacemaker. The cardioverter/pacemaker delivers, during an electrophysiology study (EP study) on a heart, a group of stimulation pulses for inducing a tachyarrhythmia. The purpose of inducing the tachyarrhythmia is to determine, under controlled circumstances, the most efficient way of terminating a tachyarrhythmia. The known cardioverter/pacemaker comprises a stimulation pulse generator, a detector for detecting the heart R-waves, a control unit, a transmitting and a receiving unit for radio waves transmitted to and from an external programmer. When an EP-study is desired the operator sets the programmer and signals are transmitted to the cardioverter/pacemaker, causing the detector to be disconnected and the stimulation pulse generator to be activated into VVT mode. Via the external programmer a sequence of pacing signals is transmitted to the stimulation pulse generator which delivers stimulation pulses to the heart synchronously with the pacing signals of the sequence. During the study the transmitting unit is also activated and transmits ECG information to the external programmer.

The sequence is mostly brief; a sequence consisting of five stimulation pulses with a time interval of 250 ms between each stimulation pulse will last just over one second. As the detector of the known cardioverter/pacemaker is disconnected during the EP-study and as the stimulation pulse generator delivers stimulation pulses controlled by the signal sequence from the programmer, the study will be fulfilled unregarding any events during the study. The stimulation pulses may not, for instance, provoke a reaction from the heart tissue and the attempt to induce a tachyarrhythmia thereby fails. It may also happen that a tachyarrhythmia with a shorter time interval than that of the sequence is induced. In such a case it would be unfortunate to deliver any further stimulation pulses to the heart.

SUMMARY OF THE INVENTION

An object of the present invention is to provide an apparatus which automatically adapts itself due to events during an EP-study, for instance when a stimulation pulse fails to provoke a reaction from the heart or when a tachyarrhythmia with a time interval that is different from the intended time interval occurs.

The above object is achieved in accordance with principles of the invention in a cardiac stimulator wherein a control device activates a time counter at the detected spontaneous heart event; a detector is activated during the delivery of the sequence, a time counter is reset each time the detector detects a spontaneous heart event, the time counter is reset and a stimulation pulse is delivered after each completed time interval, and the control device includes means for limiting the duration of the sequence.

The apparatus will, when a spontaneous heart event is detected, adapt the delivery of the next stimulation pulse in the sequence so that it will be delivered at the end of the time interval counted from the detected spontaneous heart event. If the spontaneous heart event is the result of failure of provoking a reaction by the preceding stimulation pulse the remainder of the sequence will be delivered with the selected time intervals and the probability of a successful attempt to induce a tachyarrhythmia increases. If, on the other hand, the spontaneous heart event is caused by the occurrence of a tachyarrhythmia with a higher frequency than intended no further stimulation pulses will be delivered as a spontaneous event will occur before any other time interval expires and the limiting means will break the sequence. Further it is possible, with an apparatus in accordance with the invention, to select the time intervals for the tachyarrhythmia inducing attempt so that stimulations during the vulnerable phase, which follows after a spontaneous or stimulated heart event, are avoided. It is, of course, also possible to induce a fibrillation in which case the time intervals are selected short enough to ensure stimulations within the vulnerable phase.

As mentioned above the apparatus may be used for terminating tachyarrhythmias, in particular tachycardiacs. In such a case it is possible to select the time intervals so that stimulation during the vulnerable phases is avoided.

In a preferred embodiment of the limiting means, the limiting means includes a second time counter which, when activated, counts up a preselected maximum duration for the sequence, the second time counter being activated at the same time as the sequence begins, and the control device terminating the sequence, if not already ended, when the second time counter reaches the preselected maximum duration.

The duration of the sequence thus will be limited no matter what may happen. The maximum duration may be selected to exactly correspond to the sum of the first time interval and the time intervals between the predetermined number of stimulation pulses in the sequence or it may be longer, for instance one time interval longer to allow for the whole sequence to be completed when only one spontaneous heart event occurs during the EP-study.

In another embodiment of the limiting means, the limiting means includes a time interval counter which counts the number of commenced time intervals during the delivery of the sequence and the control device terminates the sequence, if not already ended, when the number of commenced time intervals exceeds a predetermined number of time intervals.

As the number of commenced time intervals is counted the total duration for the sequence will depend on whether one or several spontaneous heart events are detected. The major advantage of this embodiment arises when a tachyarrhythmia with a higher frequency has occured, as each detected heart event will initiate a new time interval and the sequence will thereby be terminated earlier than if a maximum duration was used.

The same effect may also be achieved in an embodiment wherein the limiting means includes a spontaneous heart event counter which counts the number of spontaneous heart events detected during the delivery of the sequence and the control device decreases the predetermined number of stimulation pulses for each detected spontaneous heart event.

Because each heart reacts differently in an EP-study it is advantageous to be able to set time intervals that are either of different length or of equal length. Hereby the sequence may be adapted to the individual heart in order to optimize the probability of succeeding with the attempt to induce a tachyarrhythmia.

DESCRIPTION OF THE DRAWINGS

FIG. 1 is a schematic block diagram of a pacemaker/defibrillator constructed in accordance with the principles of the present invention.

FIG. 2 is a flowchart for limiting the duration of a sequence in the apparatus of FIG. 1.

DESCRIPTION OF THE PREFERRED EMBODIMENTS

Figure 3:
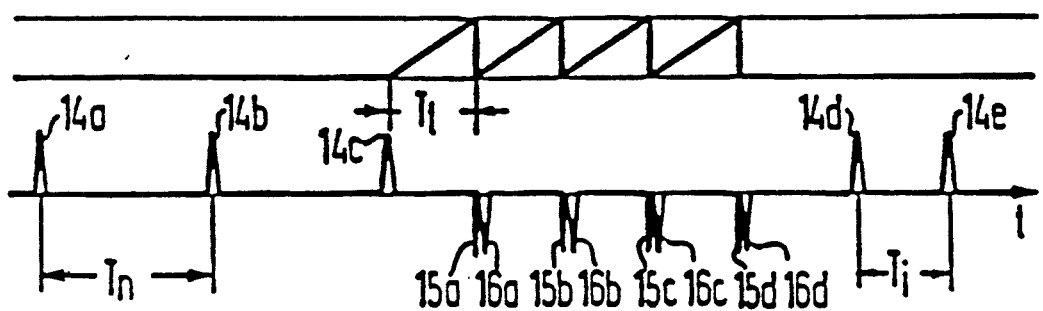
FIGS. 3, 4 and 5 respectively show time diagrams for three different attempts to induce a tachyarrhythmia.

FIG. 1 shows a block diagram for a pacemaker/defibrillator 1 which is implanted into a patient and, via an electrode lead 3, connected to the patient's heart 2 with an electrode head or a defibrillation electrode, designated as 9. The electrode lead 3 is connected to a stimulation pulse generator 4 and a detector 5 in the pacemaker/defibrillator 1. The stimulation pulse generator 4 generates stimulation pulses having a specific amplitude and duration. The stimulation pulses are delivered to the heart 2 via the electrode lead 3 and electrode head 9 with predetermined time intervals between each stimulation pulse. A programmable control device 6 controls the function of the stimulation pulse generator 4 via a control line 7.

The detector 5 detects spontaneous heart events via the electrode head 9 and the electrode lead 3 and transmits a signal to the control device 6 via a signal line 8 whenever a heart event is detected. Alternatively, the detection may be done via an electrode ring located in the vicinity of the electrode head 9 or via a separate electrode lead with a detector electrode placed in the heart 2.

In order for a physician to control and program the implanted pacemaker/defibrillator 1, the pacemaker/defibrillator 1 is provided with a telemetric unit 10 which can transmit and receive signals from an external programmer 11. The telemetry unit 10 is connected to the control device 6 via two lines 12, 13 through which signals may be transmitted to and from the telemetric unit 10.

To make it possible for the physician to decide whether a programmed stimulation pulse sequence for terminating a tachyarrhythmia is efficient or not a tachyarrhythmia is induced under controlled circumstances by means of the pacemaker/defibrillator 1. The inducing attempt takes place during an electrophysiological study (EP-study). The physician programs the pacemaker/defibrillator 1 via the programmer 11 with a suitable sequence consisting of a limited number of stimulation pulses having a specified amplitude and duration and with a specified time interval between the stimulation pulses. When the physician starts the attempt of inducing a tachyarrhythmia the detector 5 is activated and when a spontaneous heart event is detected a time counter in the control device 6 starts to run through a programmed time interval and after the lapse of the time interval the first stimulation pulse is delivered.

If no spontaneous heart events are detected during the attempt all stimulation pulses are delivered in accordance with the programming. If the attempt is successful i.e. a tachyarrhythmia has been induced, the EP-study will continue with its second part, to terminate the tachyarrhythmia. Before the study the physician has preferably programmed a terminating sequence which he judges as suitable for the patient's heart 2. When the tachyarrhythmia is induced, which the control device 6 can determine from the signals from the detector 5, the terminating sequence is delivered from the stimulation pulse generator 4 to the heart 2.

In FIG. 2 a flow chart is shown as an example of how the duration of the tachyarrhythmia inducing sequence may be limited. This limitation of the duration is necessary to avoid that the delivery of the sequence due to any unforeseen event, such as failed response from the heart or the arise of a tachyarrhythmia with a shorter time interval than that of the sequence, shall get stuck in this position. The pacemaker/defibrillator 1 could of course be constructed so that the physician could interrupt or terminate the attempt at any time, but with a pacemaker/defibrillator 1 having the limiting quality the interruption or termination may be performed in shorter time and any risk for the patient is thereby reduced.

The flow chart shows the situation as the attempt has commenced and a spontaneous heart event been detected. A counter, which in this case is implemented in the control device 6 and which counts the number n of commenced time intervals of the sequence, is reset (n=0) in the first block. The first time interval t is reset (t=0) and the counter is increased (n=n+1). A question block (n=N?) determines whether the number n of commenced time intervals has reached the preprogrammed total number N of time intervals. When this happens the sequence is terminated (END), otherwise it is determined whether the detector 5 has detected any spontaneous heart events (DET?) since the time interval t commenced. If a spontaneous heart event is detected the time interval t is reset again (t=0) and the number of commenced time intervals is increased (n=n+1). otherwise the time interval t is increased (t=t+1) and it is determined whether the time interval t has reached the preprogrammed lapse (t=$T_t$?). As long as no spontaneous heart events are detected the time interval t will be increased (t=t+1) in a loop until the time interval t reaches the preprogrammed lapse $T_t$. When the preprogrammed lapse $T_t$ is reached a stimulation pulse (STIM) is delivered, the time interval is reset (t=0) and the number n of commenced time intervals is increased (n=n+1).

Each time a spontaneous heart event is detected the time interval t will be reset (t=0) and the counter increased (n=n+1). The same will happen when the time interval lapses (t=$T_t$), following the delivery of stimulation pulse (STIM). If a tachyarrhythmia with a shorter time interval than the intended time interval $T_t$ occurs, the number n of commenced time intervals t will increase up to the preselected number N and the attempt be terminated without delivering any further stimulation pulses.

Figure 4:
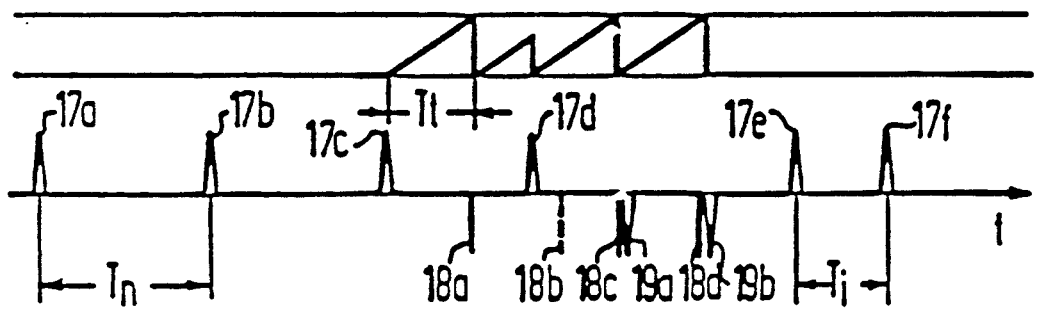
Figure 5:
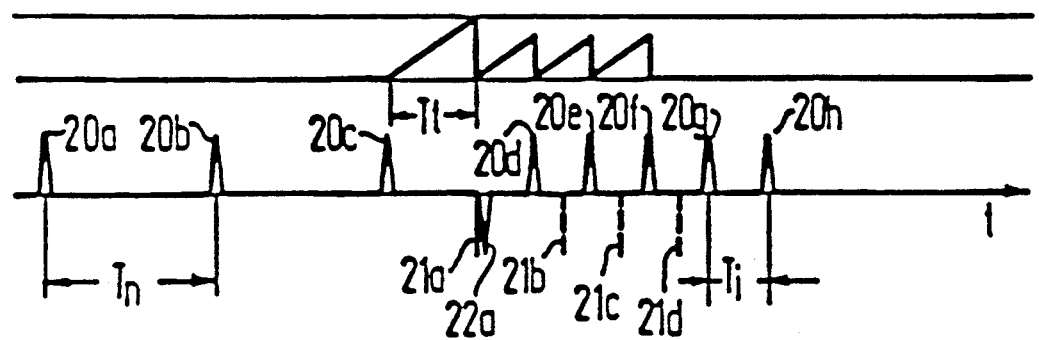

Three time diagrams are respectively shown in FIGS. 3, 4 and 5, which illustrate three different attempts of inducing a tachyarrhythmia. The figures show a time axis t with heart events (spontaneous and induced) and stimulation pulses and above the time axis t the time intervals between the stimulation pulses in the sequence are shown. On the time axis t in FIG. 3 two spontaneous heart beats 14a, 14b are shown. The spontaneous heart beats 14a, 14b have a natural time interval $T_n$. An attempt to induce a tachyarrhythmia consisting of four stimulation pulses 15a–15d with identical time intervals $T_t$ between each stimulation pulse is executed. The first stimulation pulse 15a is delivered after the lapse of the first time interval $T_t$, triggered by a spontaneous heart event 14c. Each stimulation pulse 15a–15c starts a new time interval $T_t$, after which a new stimulation pulse 15b–15d is delivered. In this example no spontaneous heart events are detected during the sequence and each stimulation pulse 15a–15d causes a stimulated heart event 16a–16d. Thereby a tachyarrhythmia with a time interval $T_i$ is induced and after the sequence the heart will beat spontaneously 14d, 14e with the induced tachyarrhythmia. The induced time interval $T_i$ is approximately of the same size as the time interval $T_t$ between the stimulation pulses in the sequence. The pacemaker/defibrillator 1 will now proceed to attempt to terminate the induced tachyarrhythmia in a way which has been programmed by the physician. This is not shown in the figure, but one possible method is described in EP-B1-108 360.

The attempt of inducing a tachyarrhythmia shown in FIG. 4 begins in the same way as the attempt in FIG. 3. A time interval $T_t$ is triggered by a spontaneous heart event 17c and when the time interval $T_t$ lapses a stimulation pulse 18a is delivered. Before the start of the sequence two spontaneous heart events 17a, 17b with a natural time interval $T_n$ are shown. Unlike the example in FIG. 3 the stimulation pulse 18a does not lead to a reaction from the heart and a spontaneous heart event 17d is detected within the time interval $T_t$ after the first stimulation pulse 18a. In an apparatus in accordance with the state of the art the following stimulation pulse would be delivered as if nothing particular had occurred, which is shown in this example with a broken line 18b, and the probability of succeeding with the attempt would decrease. Furthermore, there is the risk that the stimulation 18b would have been delivered within a vulnerable phase of the heart. Such vulnerable phases always occur after a spontaneous or stimulated heart event. In the pacemaker/defibrillator 1 according to the invention the time interval $T_t$ will be reset and start again from zero when the spontaneous heart event 17d is detected. The second stimulation pulse 18c will hereby be delivered after the lapse of the time interval $T_t$ counted from the point in time when the spontaneous heart event 17d was detected. The second stimulation pulse 18c causes a response from the heart in form of a stimulated heart event 19a and a new time interval $T_t$ commences. Also the third stimulation pulse 18d results in a stimulated heart event 19b and a tachyarrhythmia has been induced. The heart beats spontaneously 17e, 17f with the induced time interval Ti, which is of approximately the same size as the time interval $T_t$ between the stimulation pulses 18a–18d.

In FIG. 5 the inducing attempt begins after two spontaneous heart events 20a, 20b, as in FIGS. 3 and 4, with a time interval $T_t$ triggered by a spontaneous heart event 20c. The first stimulation pulse 21a causes a stimulated heart reaction 22a and starts a new time interval $T_t$. In this example a tachyarrhythmia with a time interval $T_i$ that is shorter than the time interval $T_t$ between the stimulation pulses occur. In an apparatus in accordance with the state of the art the delivery of the rest of the stimulation pulses in the sequence would continue regardless of the arisen tachyarrhythmia. The pacemaker/defibrillator 1 according to the invention, however, proceeds differently. As the first spontaneous heart event 20d occurs before the lapse of the interval $T_t$ after the first stimulation pulse 21a, the time interval $T_t$ will be reset and start again without the pacemaker/defibrillator 1 delivering the second stimulation pulse 21b. Since the arisen tachyarrhythmia has a shorter time interval $T_i$ than the time interval $T_t$ in the sequence, the next spontaneous heart event 20d will again occur before the time interval $T_t$ has lapsed. This is repeated for each commenced time interval $T_t$ and hereby no further stimulation pulses will be delivered during the attempt. In FIG. 5 designations 21b–21d mark the places where stimulation pulses would have been delivered if the preceding spontaneous heart event 20d–20f had not occurred. The packemaker/defibrillator 1 can now proceed to attempt to terminate the tachyarrhythmia.

In the three given examples in FIGS. 3–5 the sequence consists of four equidistant stimulation pulses. This is not necessary. In some cases it may be easier to induce a tachyarrhythmia by having successively shorter time intervals between the stimulation pulses and in other cases another division may be suitable. The number of stimulation pulses in an EP-study may also vary, much depending on whether it is easy or difficult to induce a tachyarrhythmia in the patient's heart.

In similar ways, as described in connection with the figures, the pacemaker/defibrillator 1 can also be used for terminating a tachyarrhythmia. When attempting to terminate a tachyarrhythmia, a time interval that is sufficiently large to avoid stimulation during the vulnerable phase should be selected.

It is the intention of the inventor to embody within the patent warranted hereon all changes and modifications as reasonably and properly come within the scope of the inventors' contribution to the art.

I claim as my invention:

1. An implantable medical device for stimulating a heart comprising:
   stimulation pulse generator means for generating and delivering stimulation pulses in vivo to cardiac tissue;
   activatable detector means for, when activated, detecting spontaneous cardiac events;
   control means connected to said stimulation pulse generator means and to said detector means for inducing or terminating a tachyarrhythmia by causing said stimulation pulse generator means, following a time interval after the detection of a spontaneous cardiac event by said detector means, to deliver a sequence of a predetermined number of stimulation pulses with said time interval between each pulse, and said control means activating said detector means during delivery of said sequence;
   said control means including time counter means for beginning a time count upon the detection of each spontaneous cardiac event by said detector means and said control means causing said stimulation pulse generator means to deliver a stimulation pulse when said time counter means reaches a time count equal to said interval;

means for resetting said time counter means upon the detection of another spontaneous cardiac event during said time interval by said detector means and upon the delivery of a stimulation pulse by said stimulation pulse generator means; and said control means including means for limiting the duration of said pulse sequence.

2. An implantable medical device as claimed in claim 1, wherein said means for limiting the duration of said sequence includes a second time counter means in said control means for beginning a further time count at a beginning of said sequence and for generating a signal causing said control means to terminate said sequence if said second time counter means reaches a predetermined maximum duration.

3. An implantable medical device as claimed in claim 1, wherein said means for limiting the duration of said sequence includes a time interval counter means for counting the number of said time intervals during the delivery of said sequence and for generating a signal causing said control means to terminate said sequence if the number of time intervals counted by said time interval counter means exceeds a predetermined number.

4. An implantable medical device as claimed in claim 1, wherein said means for limiting the duration of said sequence includes a spontaneous heart event counter means for counting the number of said spontaneous heart events detected by said detector means during the delivery of said sequence and for generating a signal causing said control means to decrease said predetermined number of stimulation pulses for each detected spontaneous heart event.

5. An implantable medical device as claimed in claim 1, wherein said control means includes means for changing the length of said time intervals in a sequence.

6. An implantable medical device as claimed in claim 1, wherein said control means includes means for maintaining said time intervals the same length during a pulse sequence.

7. A method for inducing or terminating tachycandia comprising the steps of:

detecting in vivo spontaneous cardiac events;

delivering in vivo, following a time interval after detecting a spontaneous cardiac event, a sequence of a predetermined number of stimulation pulses with said time interval between each pulse;

activating a time counter to begin a time count upon the detection of each spontaneous cardiac event;

delivering a stimulation pulse when said time count reaches a value equal to said time interval;

resetting said time counter upon the detection of another spontaneous cardiac event during said time interval and upon the delivery of a stimulation pulse; and limiting the duration of said pulse sequence.

8. A method as claimed in claim 7, wherein the step of limiting the duration of said pulse sequence is further defined by the steps of:

activating a second time counter at a beginning of said pulse sequence; and terminating said sequence if said second time counter reaches a preselected maximum duration.

9. A method as claimed in claim 7, wherein the step of limiting the duration of said pulse sequence is further defined by the steps of:

activating a time interval counter which counts the number of said time intervals during the delivery of said sequence; and terminating said sequence if the number of counted time intervals exceeds a predetermined number.

10. A method as claimed in claim 7, wherein the step of limiting the duration of said sequence is further defined by the steps:

counting the number of said spontaneous heart events during the delivery of said sequence; and decreasing said predetermined number of stimulation pulses for each detected spontaneous heart event which is counted.

11. A method as claimed in claim 7, comprising the additional step of varying said time intervals in said sequence.

12. A method as claimed in claim 7, comprising the additional step of maintaining said time intervals in said sequence of the same length.

* * * * *